United States Patent [19]

Fischell et al.

[11] Patent Number: 4,524,773

[45] Date of Patent: Jun. 25, 1985

[54] APPARATUS FOR INHIBITING SELF-INJURIOUS BEHAVIOR (SIB) IN PATIENTS

[75] Inventors: Robert E. Fischell, Silver Spring; Arnold L. Newman; Henry B. Riblet, both of Kensington; William R. Powell, Columbia, all of Md.

[73] Assignee: The John Hopkins University, Baltimore, Md.

[21] Appl. No.: 843,944

[22] Filed: Aug. 24, 1983

[51] Int. Cl.³ .............................................. A61N 1/38
[52] U.S. Cl. .................................. 128/419 S; 128/421
[58] Field of Search ................ 128/1.5, 419 R, 419 S, 128/421, 422, 423 R, 424

[56] References Cited

U.S. PATENT DOCUMENTS 3,834,379  9/1974  Grant ................................ 128/419 S
3,850,161  11/1974  Liss ................................. 128/419 S
3,918,461  11/1975  Cooper ............................... 128/422
4,440,160  4/1984  Fischell et al. ................... 128/419 S Primary Examiner—William E. Kamm
Attorney, Agent, or Firm—Robert E. Archibald; Howard W. Califano

[57] ABSTRACT

An improved apparatus for inhibiting self-injurious behavior (SIB) in patients includes a stimulus module for generating and applying an aversive electrical stimulation to the patient's skin and a sensor module and/or remote actuator for actuating the stimulus module in response to a patient's self-injurious behavior. The apparatus uses a near field magnetic link to transmit a coded signal from a sensor module or from a remote actuator to the stimulus module worn on the patient. The stimulus module uses a unique flyback circuit design and the electrical stimulation is tuned to achieve a maximum physiological response with minimal power drain.

18 Claims, 9 Drawing Figures

APPARATUS FOR INHIBITING SELF-INJURIOUS BEHAVIOR (SIB) IN PATIENTS

BACKGROUND OF THE INVENTION

1. Field of the Invention

The invention relates to an improved apparatus for preventing self-injurious behavior in patients. The invention uses a near field magnetic link to transmit a coded signal from a sensor module or from a remote actuator to a stimulus module worn on the patient. The stimulus module uses a unique flyback circuit design to generate an electrical stimulus which is tuned to achieve a maximum physiologic response with minimal power drain.

2. Description of Contemporary or Prior Art

The use of aversive stimulation to prevent certain types of behavior is known in the art. U.S. Pat. No. 3,998,209, issued to Gilbert Macvaugh on Dec. 21, 1976, teaches the application of electric shock pulses for conditioning snoring. U.S. Pat. No. 3,885,576, issued to Elliott Symmes, on May 26, 1975, teaches the use of electric shock as a means to deter smoking. In that patent a mercury switch is mounted on a wrist band so that when the user moves his arm (e.g., to place a cigarette in his lips), the mercury switch closes and allows an electric current to flow to electrodes on the user's wrist band.

The use of aversive stimulation to inhibit self-injurious behavior was first described by Mooza Grant in U.S. Pat. No. 3,834,379, issued Sept. 10, 1974. Mooza Grant describes an apparatus which conditions self-destructive patients against self-injurious blows to the head. The apparatus contains a helmet which is mounted on the patient's head to absorb self-injurious blows. The helmet contains a metallic cylinder and a movable pin disposed centrally therein. When a patient strikes the helmet, the pin contacts with the cylinder and establishes an electrical contact which activates an electronic package (described as being disposed within a jacket in patients clothes). An electric pulse generated in the electronic package is sent to the electrodes contained in an arm band and provides an aversive electric shock to the patient's arm. The helmet, electronic package, and stimulation electrodes are all connected by electrical wires.

The use of a wireless communication link between a sensor module and a stimulus module was first described by R. E. Fischell et al in U.S. Pat. No. 4,440,160, issued Apr. 3, 1984. The Fischell et al apparatus includes a means for setting an acceleration threshold so that an aversive blow to the head can be distinguished from acceleration due to the patient's regular activities. The Fischell et al device teaches the use of an event counter located in both the sensor and stimulus modules to record the occurrence of both a self-injurious blow and the application of aversive stimulation.

SUMMARY OF THE INVENTION

The present apparatus contains novel improvements not found in the prior art. The invented apparatus contains a unique magnetic communication link and a unique electrical stimulation circuit. Since the sensor and stimulus modules are worn on the patient, reduction in size of the sensor and stimulus modules would allow the patient to perform "normal" activities without interference from a bulky body-worn module. Reduction in size has placed strict power optimization requirements on both the sensor and stimulus modules. The stimulation circuit contains a unique energy transfer circuit using a flyback transformer design that efficiently transfers energy from a small battery to a charging capacitor that provides the aversive stimulation. To further optimize power consumption, the electrical stimulation waveform is physiologically tuned to the natural frequency of nerve receptors to provide a maximum aversive stimulation waveform with minimum power consumption.

The invention also incorporates a unique near-field communication link. Because a near field magnetic signal is not a propagating signal, communications to each patient can be isolated. In addition, the near-field magnetic signal is modulated to contain digitally coded information which uniquely identifies each patient. When the stimulus module matches the received digital code with the patient's identification code, which is stored in memory, only then is an aversive electrical stimulation generated. Isolating each patient's behavior is important because institutionalized SIB (Self-Injurious Behavior) patients are often close to each other when playing or interacting in the same room. It is extremely important that a particular patient receives aversive stimulation only because of his own self-injurious behavior.

Similarly, the communication link must be reliable—failure to provide electrical stimulation for each self-injurious episode could also be damaging to the patient's treatment. The communication link described in this application includes a transmitting magnetic coil that is controlled by digital logic. This unique design uses a third harmonic filter that eliminates the higher frequency components of the square wave and converts these digital pulses into a sine wave. This efficiently couples power to the transmitting magnetic coil. To increase the communication link's reliability, the receiver uses two orthogonally arranged receiving magnetic coils that are inductively coupled to the transmitting magnetic coil. This unique feature reduces the size of the receiver's null areas and assures that reliable communication is maintained irrespective of the orientation between the stimulus module and the sensor module.

One novel feature of the invented apparatus is the use of a near-field magnetic communications link which allows isolated communication to each patient.

A second novel feature is the use of a coded magnetic field which contains a unique digital code identifying each patient. This feature assures that the aversive stimulation of institutionalized patients housed in close proximity can be isolated.

A third novel feature of the invented apparatus is the use of a unique energy transfer circuit, incorporating a flyback transformer, to efficiently transfer energy from a small battery to a charging capacitor. The charging capacitor provides the aversive electrical stimulation at high voltage.

A fourth novel feature of the invented apparatus is the use of a stimulus circuit that provides a physiologically tuned electrical stimulus for a maximum aversive stimulation with minimal power consumption.

A fifth novel feature of the invented apparatus is the use of a near-field magnetic communication link which is directly controlled by digital logic.

A sixth novel feature of the invented apparatus is the use of a third harmonic filter as part of the transmitting means to eliminate the Fourier squaring component, so that digitally produced squarewave pulses can efficiently drive a magnetic transmitting coil with a sine wave.

A seventh novel feature of the invented apparatus is the use of a pair of orthogonally oriented receiving magnetic coils to inductively link with the magnetic transmitting coil. This feature reduces the size of the magnetic null and assures a more reliable communication link.

The above-mentioned features, as well as other features and advantages of the present invention, will become readily apparent from the following description of several non-limiting illustrative embodiments and the accompanying drawings.

DESCRIPTION OF THE PREFERRED EMBODIMENT

Figure 1:
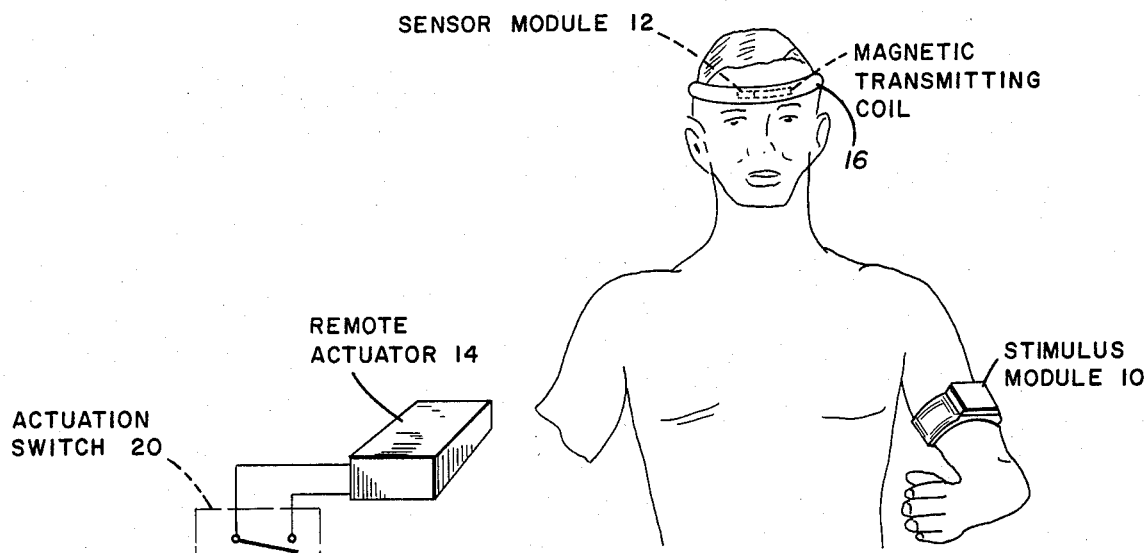
FIG. 1 is an illustration of a person wearing the invented self-injurious behavior inhibiting systems with an optional remote actuator.

An improved apparatus for inhibiting self-injurious behavior is illustrated in FIG. 1. The apparatus is generally composed of a stimulus module 10 and a sensor module 12 and/or a remote actuator 14. The sensor module 12 is mounted on the patient's body and detects a self-injurious blow to that body member. As shown in FIG. 1, the sensor module can be mounted on a headband 16 to detect blows to the patient's head. (It is to be understood that the sensor module could be mounted on an elastic elbowband, kneeband, ankleband, wristband, etc.) When the self-injurious behavior is detected by the sensor module 12, a coded magnetic signal is emitted by magnetic transmitting coil 18. The coded magnetic signal contains an ID code unique to the particular patient. The stimulus module 10 contains a receiver means which detects the near-field magnetic emission from magnetic transmitting coil 18 and processes the coded data. If the received coded data matches the ID code, the stimulus module generates a controlled aversive electrical stimulation which is applied to to the patient's skin. The remote actuator 14 can be used in conjunction with or independent of sensor module 12. The remote actuator 14 contains a transmitter means which generates a coded magnetic field which is detected by the stimulus module 10. An actuation switch 20 can be closed by an attendant which will trigger the transmission of the coded magnetic signal that, when received and identified by the stimulus module 10, will cause a controlled aversive electrical stimulation to be generated.

Figure 2:
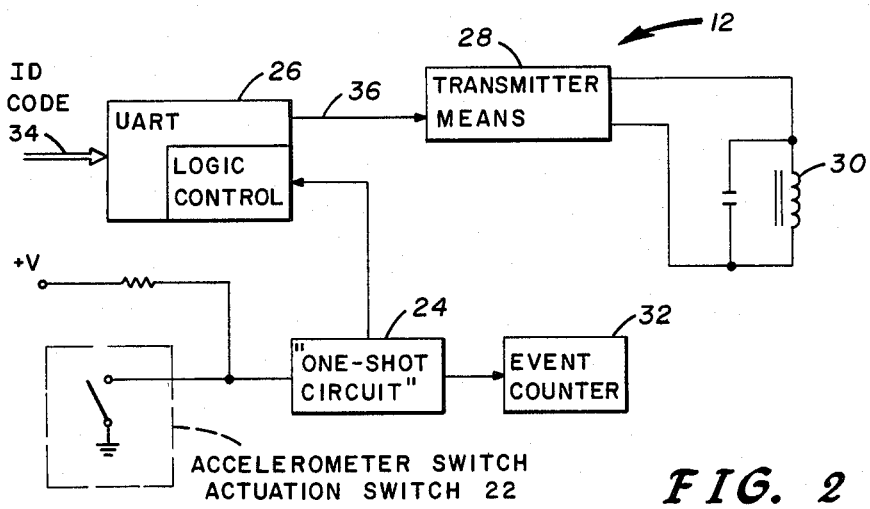
FIG. 2 is a block diagram of the sensor module and/or the remote actuator.

FIG. 2 is a block diagrammatic view of the sensor module 12. The sensor module generally includes: an accelerometer switch 22, a "one-shot" circuit 24, a UART (Universal Asynchronous Receiver/Transmitter) 26, a transmitter means 28, a near-field magnetic transmission coil 30 and an event counter 32. The accelerometer switch 22 switches at a preselected acceleration threshold. The acceleration threshold is set to distinguish "normal" acceleration from a self-injurious blow. (A threshold level between two g's and 5 g's can be selected as values large enough to avoid aversive stimulation as a result of acceleration experienced in normal activity, and yet small enough to detect a non-damaging impulse to the head.) When the acceleration switch is closed by a self-injurious blow, current triggers the "one-shot" circuit 24. The "one-shot" circuit in turn actuates an event counter 32 and UART 26. For each patient, a unique ID code 34 is loaded into the UART. When actuated by the "one-shot" circuit 24, the UART 26 converts the parallel input data code 34 into a serial data code which is sent along line 36 to transmitter means 28. Transmitter means 28 is switched by the serial data code sent along line 36 and in turn drives magnetic transmitting coil 30 to generate a coded alternating magnetic field. The block diagram of FIG. 2 also describes the electronics of the remote actuator 14, with the only difference that the accelerometer switch 22 is replaced by an actuation switch 20.

Figure 3:
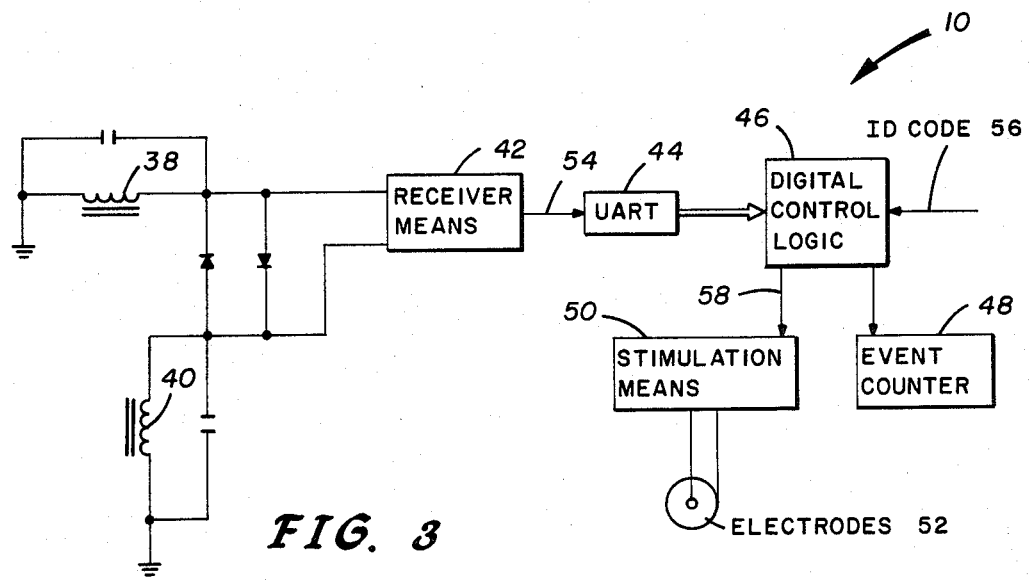
FIG. 3 is a block diagram of the stimulus module.

FIG. 3 is a block diagrammatic view of the stimulus module 10. The stimulus module 10 generally includes: two orthogonal receiver coils (38, 40), a receiver means 42, a UART 44, digital control logic 46, and event counter 48, a stimulation means 50, and a pair of electrodes 52. The two orthogonal coils (38, 40) are inductively coupled to magnetic transmitting coil 30 by a near field magnetic phenomena. The two orthogonal coils (38, 40) receive the coded magnetic field and send electrical impulses to receiver means 42. The two receiver coils (38, 40) are arranged orthogonally to reduce the receiver null. The receiver means 42 detects and processes the electrical impulses received by the orthogonal coils (38,40), and extracts the serial data code. The serial data code is sent along line 54 to UART 44. UART 44 converts the serial data into a parallel code which is sent along a parallel bus to digital control logic 46. The digital control logic 46 compares the received digital code with an ID code 56 unique to the particular patient. If the received code matches the ID code, the digital control logic triggers event counter 48 and sends enabling pulses along line 58 to stimulation means 50. The stimulation means responds to the enabling pulses and generates an electrical voltage which is applied to the patient's skin via electrodes 52. The digital control logic 46 controls the intensity and duration of electrical stimulation by determining the number and timing of enabling pulses sent along line 58.

Figure 4:
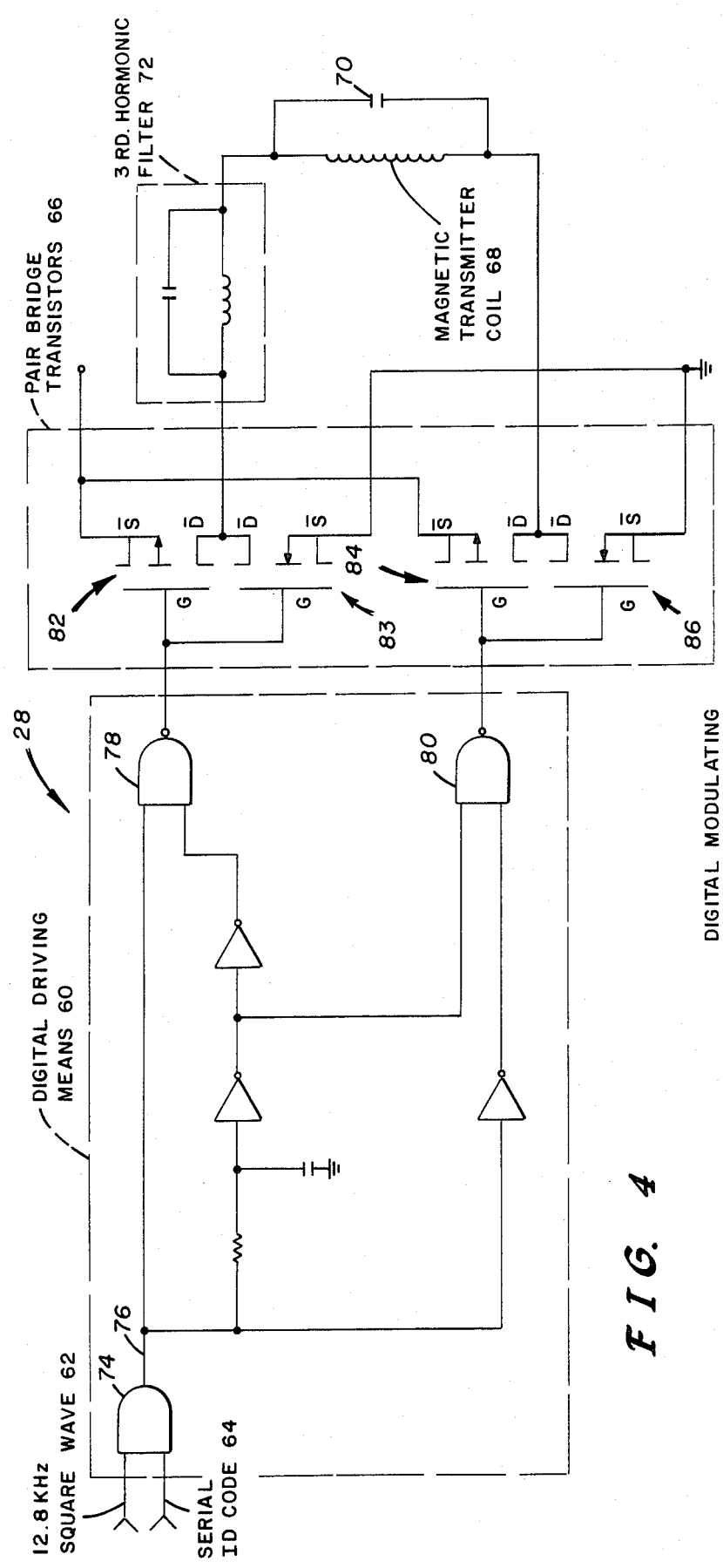
FIG. 4 is a schematic diagram of the near field magnetic transmitting means.

The transmitter means 28, best shown in FIG. 4, uses digital logic to directly generate a coded magnetic field. The transmitter means 28 generally includes: a digital driving means 60 which receives as input a 12.8 kHz square wave carrier signal 62 and a digital modulating ID code 64; a pair of bridge transistors 66 which are alternatively switched "ON" and "OFF" by the digital driving means 60; a magnetic transmitting coil 68 which is tuned by a capacitor 70 to resonance at the carrier frequency; and, a third harmonic filter 72 which converts a square wave switching signal generated by the digital driving means 60 into a sine wave which drives the magnetic transmitting coil 70.

Figure 5:
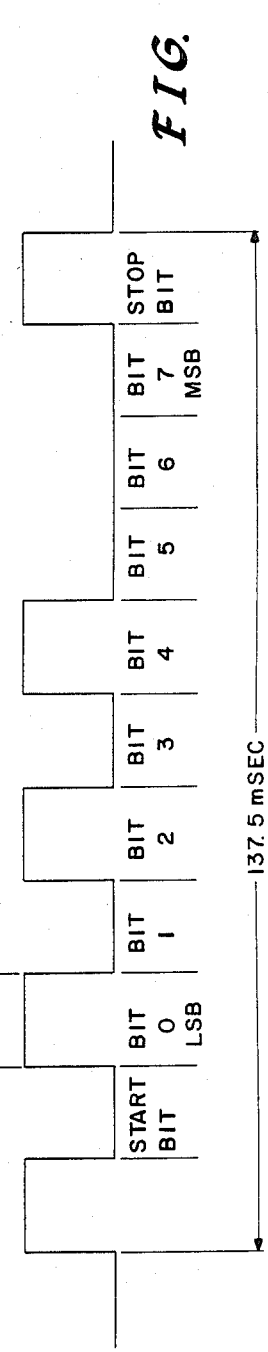
FIG. 5 illustrates the transmitted identification code.

The AND gate 74 of the digital driving means 60 receives a 12.8 Khz square wave carrier 62 and a digitally modulated ID code 64. The digitally modulating ID code 64, shown in FIG. 5, is a serial code containing start bit, an 8-bit code and a stop bit. Each patient has their own unique ID code so that each patient's behavior can be individually controlled. This is important because the institutionalized SIB patients are usually housed in close proximity to each other and may be playing or interacting in the same room. Output 76 from AND gate 74 is normally low. When a SIB event occurs, digitally modulating code 64 is generated causing AND gate 74 to switch, thereby producing a series of 12.8 kHz square wave groupings (i.e., the 12.8 kHz square wave carrier 62 is modulated by the digital modulating code 64.)

The modulated 12.8 kHz carrier 76 causes NAND gates 78 and 80 to go low in an alternating manner. (The NAND gates 78 and 80 are normally held high.) Switching NAND gates 78 and 80 in this manner causes two complementary pairs of P&N channel MOSFETS 66 arranged in bridge formation to switch current in alternating directions through magnetic transmitting coil 70. When NAND gate 78 is "low" and NAND gate 80 is "high" transistors 82 and 86 will be "ON" and transistors 83 and 84 will be "OFF"—causing current to flow down through magnetic transmitting coil 70. When NAND gate 78 is "high" and NAND gate 80 "low", transistors 83 and 84 will be "ON" and transistors 82 and 86 will be "OFF"—causing current to flow up through magnetic transmitting coil 70. In this manner, an alternating 12.8 kHz magnetic field is generated by magnetic transmitting coil 70.

The digital driving means 60 and the bridge transistors 66 directly drive the transmitting coil 70. In other words, the transmitting coil is directly driven by digital logic, and with the use of MOSFET transistors there is no need for amplification between the logic circuit and the bridge transistors. A third harmonic filter 72 is used to convert the digital square wave signal to a sine wave. The third harmonic filter uses Fourier subtraction to eliminate the primary squaring component of the square wave. Thus, a unique transmitter circuit is provided that allows a magnetic transmitting coil 70 to be directly driven by digital logic.

Figure 6:
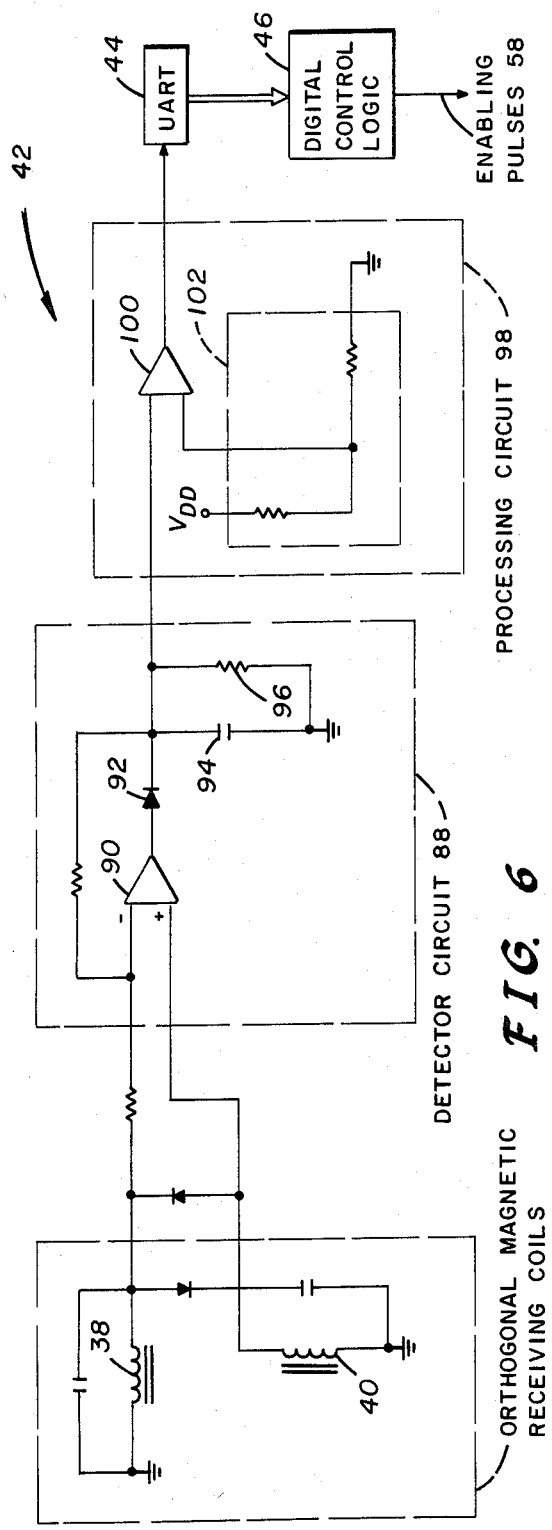
FIG. 6 is a schematic diagram of the near field magnetic receiving means.

The magnetic transmitting coil 70 generates a near field magnetic signal which inductively couples the transmitting coil 70 to a receiving means 42, best shown in FIG. 6. Near field magnetic coupling is used, as opposed to a radiating electromagnetic field, because it provides increased isolation, so that each SIB patient's behavior can be individually modified.

The receiving means 42, shown in schematic form in FIG. 6, receives the near field magnetic signal generated by the transmitting means 28, and detects and processes the signal to recover the digital modulating ID code 64 (shown in FIG. 5). The receiver means 42 generally includes: a pair of orthogonal receiving coils (38, 40) to magnetically couple with the near field magnetic signal generated by the transmitter means; a detector circuit 88 which includes a differential operational amplifier 90, a diode 92, capacitor 94 and resistor 96; and, a processing circuit 98 to further "square" the recovered digital signal.

Two orthogonal coils (38, 40) are used to reduce the receiver's null positions and to allow a greater range of angular positioning between the transmitter means and a receiver means. A certain voltage is induced in the two coils from the near magnetic field signal. The OP amp 90 performs an algebraic addition of the voltage received by each coil. If the stimulus module containing the receiver means is mounted on the SIB patient's arm, this novel orthogonal coil arrangement assures a strong communication link regardless of arm position or motion. It is to be understood that the use of three orthogonal coils would further reduce the receiver's null position.

The detector circuit 88 extracts a digital code from the modulated 12.8 kHz signal received by the orthogonal coils (38, 40). Diode 92, capacitor 94 and resistor 96 work in combination using known detection techniques to extract the digital code from the electrical signal. The detected digital code, in serial form, then goes to processing circuit 98 where a comparator 100 "squares up" the detected code by comparing the detected digital code with a voltage reference 102. The comparator circuit provides a certain degree of noise immunity.

The detected digital code is then sent to a UART 44 where the serial code is converted into a parallel code format. The parallel format is compared by digital control logic 46, by known digital techniques, to determine if the detected digital code matches the identifying code for that particular receiver. If a match occurs, enabling pulses are sent along line to the stimulation means 50.

Figure 7:
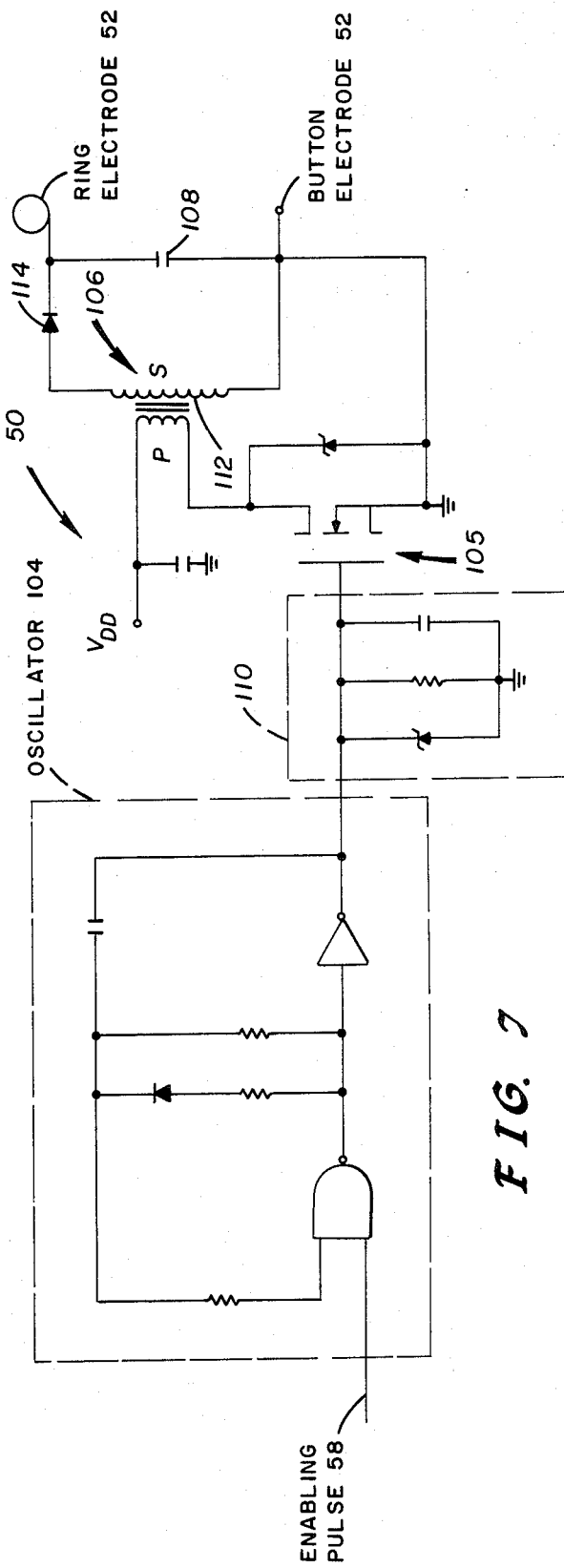
FIG. 7 is a schematic diagram of the stimulus means.

Stimulation means 50, shown in FIG. 7, is enabled when enable line 58 goes "HIGH". In the preferred embodiment digital control logic means 46 generates a series of 80 kHz square wave enabling pulses signal along line 58 for a controlled period of time when the detected digital code matches the receiver's ID code. The stimulation means 50 generally includes: an oscillator 104 triggered by the squarewave enabling pulses sent along line 58; a transistor 106 which is turned "ON" and "OFF" at a high frequency by oscillator 104; a flyback transformer circuit 106 which is used to incrementally charge capacitor 108. As shown in FIG. 7, oscillator 104 is a free running astable oscillator in the form of a cross-coupled gate oscillator. (However, other oscillator designs could be substituted.) During the period when enable line 58 is "HIGH" the oscillator 104 generates a 125 kHz signal which triggers transistor 106. (Frequencies other than 125 kHz can be used. Circuit elements 110 are used to protect the gate of transistor 106.)

Transistor 105 can be any bipolar type switching transistor, although the inventors prefer to use a MOSFET because of its low "on resistance". When transistor 105 is "ON", current flows from $V_{DD}$ through the primary of transformer 112 to ground, producing a magnetic field. Because of diode 114, the generated magnetic field will not cause a current flow into the secondary circuit. However, when transistor 105 is turned "OFF" the collapsing magnetic field in the primary induces a current in the opposite direction in the transformer's secondary circuit. The diode 114 allows current to flow in the clockwise direction and to charge capacitor 108. (The preferred embodiment uses a small cup core 1:2 step-up transformer, although other equivalent transformers could be substituted.) The resulting flyback transforming circuit arrangement provides a very efficient energy transfer from the battery (9 volts) to the charging capacitor 108. Each time oscillator 104 causes transistor 105 to switch, a small increment of energy is efficiently pumped into capacitor 108. During the 80 Hz "High" enable pulse generated over line 58, a total of 781 pulses (125 kHz) of charge will be pumped rapidly into capacitor 108. Voltage stored in capacitor 108 is discharged through the ring and button electrode combination 52 into the patient's skin. The SIB patient's skin closes the circuit across the ring and button electrode combination and an aversive electrical shock is introduced into the nervous system of the patient.

Figure 8:
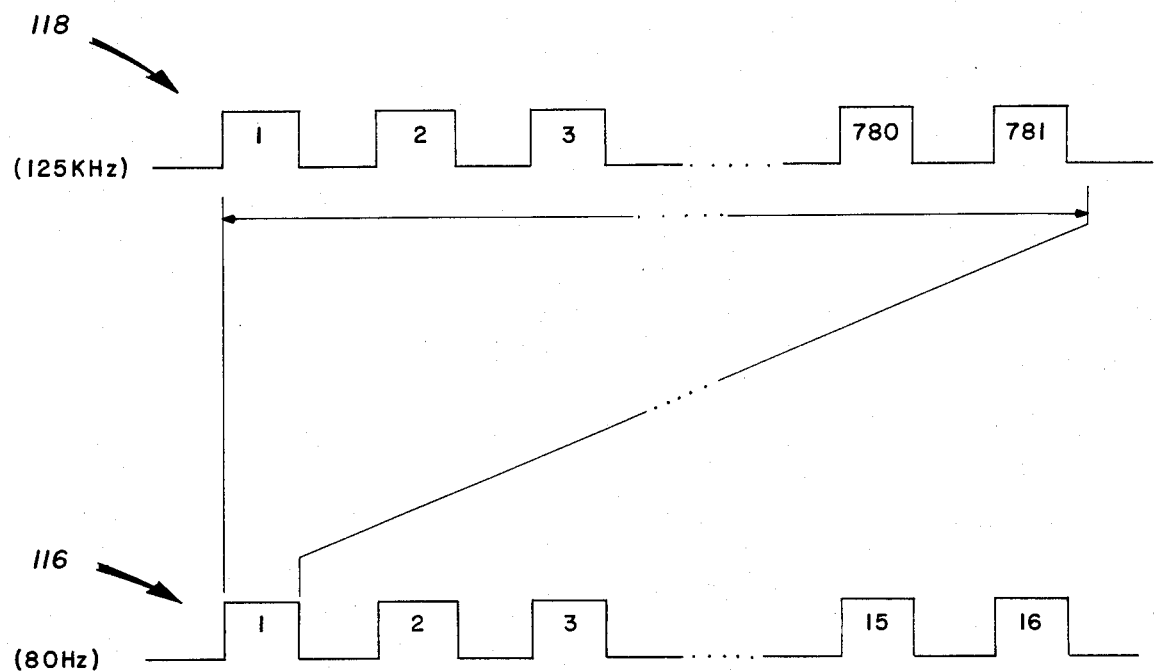
FIG. 8 is a diagram illustrating the signal structure of the electrical stimulation.

FIG. 8 shows pulses generated by oscillator 104 and used to pump the flyback transformer circuit 106 during a 200 millisecond aversive stimulus episode. Pulse train 116 is composed of sixteen pulses, generated at a frequency of 80 Hz, which enables oscillator 104. During each "High" enable pulse oscillator 104 generates 781 square wave pulses at a frequency of 125 kHz (pulse train 118). Each of the 781 squarewave pulses cause the flyback circuit 106 to pump energy into capacitor 108.

Figure 9:
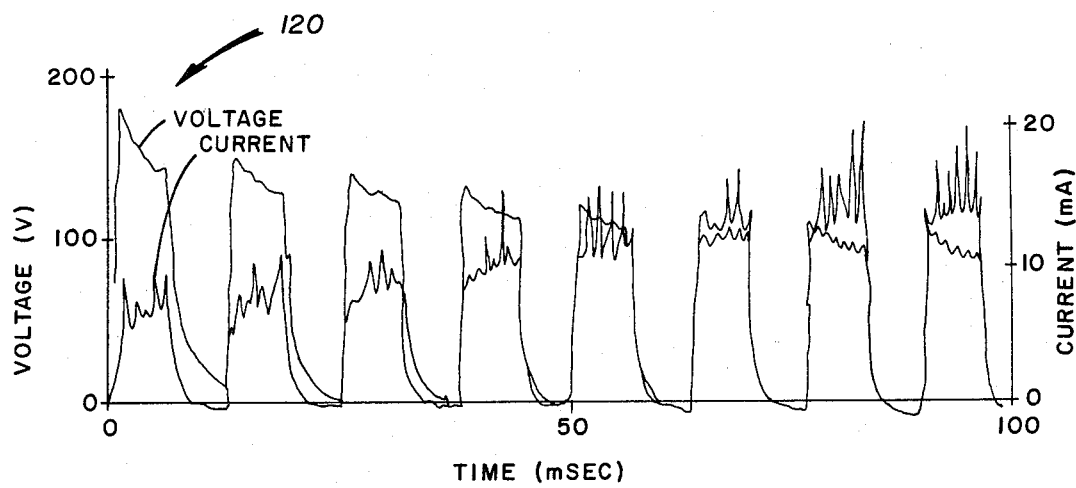
FIG. 9 is a graph illustrating the voltage and current characteristics of the train of pulses generated by the stimulus module.

FIG. 9 shows the voltage and current characteristics of aversive stimulation as capacitor 108 discharges via the ring and button electrode into the patient's skin. Aversive output pulses 120 occur at the same rate as the squarewave enabling pulses generated along line 58 (see FIG. 7). Therefore, by tunning the frequency of the enabling pulses one can adjust the frequency of the aversive output pulses. Looking at the first aversive output pulse shown in FIG. 9, we observe that the voltage is initially high and the current is initially low. With a large dv/dt the skin impedance will break down and the current will increase. (The stimulation means is designed to provide an initial high dv/dt which breaks down the skin impedance so that energy can be more effectively delivered into the patient's skin.) As the skin impedance continues to decrease, current flows more rapidly from capacitor 108 and the voltage level slowly drops.

The frequency of the aversive output pulses can be adjusted by adjusting the frequency of the enabling pulse sent along line 58. Nerve receptors in the skin have a limited refractory time. It was determined that if aversive pulses occurred faster than 100 Hz, no additional pain is experienced. The nerve receptors are unable to respond faster than 100 Hz. Therefore, providing aversive output pulses faster than 100 Hz doesn't produce any additional aversive pain but will consume valuable battery power. By adjusting the frequency of the enabling pulses sent along line 58, one can tune the aversive circuit to the inherent limitations of the nervous system. It was found that an enabling frequency of 60 to 100 Hz produces desirable results.

The intensity of the aversive stimulus can also be controlled by adjusting the total energy delivered to the patient's skin. The present invention accomplishes this by decreasing the total number of pulses of aversive stimulation delivered. The inventors have found that sixteen pulses of aversive stimulation (shown in FIG. 9), will produce a high intensity of pain and eight pulses of aversive stimulation will produce a moderate intensity of pain. By adjusting the number of pulses delivered in any aversive stimulation episode, the intensity of pain can be adjusted. (It is to be understood that digital control logic 46 controls the number and characteristics of the enabling pulses sent along line 58, which in turn adjusts the total number of aversive output pulses generated by the stimulation means.) It is also to be understood that it is within the contemplation of the invention to use other methods to reduce the total delivered energy. The frequency of the enabling pulses or the oscillator 104 frequency can be adjusted; the number of pulses delivered can be adjusted; or, a variable resistor can be placed across charging capacitor 108 and the output voltage can be adjusted.

Obviously many modifications and variations of the present invention are possible in light of the above teachings. It is therefore to be understood that within the scope of the appended claim the invention may be practiced otherwise than is specifically described.

What is claimed and desired to be secured by letters patents of the United States is:

1. An apparatus for inhibiting self-injurious behavior, comprising:
an actuator means for generating a modulated near field magnetic signal in response to a patient's self-injurious behavior, said modulated near field magnetic signal being modulated with coded information identifying said patient; and
a stimulus module, adapted to be worn on said patient's body, including:
  a receiver means for receiving said modulated near field magnetic signal and for detecting and processing said coded information;
  a digital control means, operably connected to said receiver means, for generating an enabling command when said coded information detected by said receiver means matches with a stored identification code; and,
  a stimulation means, operably connected to said digital control means, for generating pulses of aversive electrical stimulation to be applied to said patient's skin, in response to said enabling command.

2. The apparatus of claim 1, wherein said stimulation means further comprises a flyback transformer circuit means for pumping energy from a battery into a capacitor, said capacitor discharging through electrodes adapted to be placed against said patient's skin.

3. The apparatus of claim 2, wherein said flyback transformer circuit means is triggered by an oscillator, each pumping pulse from said oscillator causing said flyback transformer circuit means to pump energy from said battery into said capacitor, and wherein said oscillator is actuated by said enabling command generated by said digital control means.

4. The apparatus of claim 3, wherein said enabling command generated by said digital control means is a series of enabling pulses, said oscillator being actuated to generate pumping pulses during the pulse width of each of said enabling pulses.

5. The apparatus of claim 4, wherein the frequency of said enabling pulses is selected to match the inherent frequency response of pain receptors.

6. The apparatus of claim 5, wherein the frequency of said enabling pulses is selected from the range 50–100 kHz.

7. The apparatus of claim 4, wherein the member of said enabling pulses generated by said digital control means is controlled to adjust pain intensity.

8. The apparatus of claim 7, wherein the member of said enabling pulses is selected from the range 2–20 pulses, wherein such enabling pulses are 80 Hz square wave pulses.

9. The apparatus of claim 1, wherein said receiver means comprises:
two orthogonal magnetic receiving coils for receiving said modulated near field magnetic signal; and,
a detection circuit, operably connected to said two orthogonal magnetic receiving coils, for detecting said coded information.

10. The apparatus of claim 9, wherein said receiver means further comprises:
a processing circuit, operably connected to said detection circuit, for squaring said coded information detected by said detection circuit.

11. The apparatus of claim 10, further comprising a UART, operably connected to said receiver means, for converting said coded information processed by said processing circuit into a parallel format which is inputed to said digital control means.

12. The apparatus of claim 1, wherein said actuator means comprises:
a magnetic transmitting coil;
a transmitter means, operably connected to said magnetic transmitting coil, for driving said magnetic transmitting coil with a carrier signal modulated by said coded information, wherein said coded information is a series of digital pulses.

13. The apparatus of claim 12, wherein said transmitter means comprises:
a pair of bridge transistors, operably connected to said magnetic transmitting coil, for driving current pulses in an alternating manner through said magnetic transmitting coil;
a third harmonic filter means, operably connected in series with said magnetic transmitting coil, for reducing the Fourier squaring component from said driving current pulses; and,
a digital driving means for modulating a square wave carrier signal with said series of digital pulses and for alternatively switching said pair of bridge transistors in accordance with said modulated square wave carrier signal.

14. The apparatus of claim 13, wherein said pair of bridge transistors is a complimentary pair of PN MOSFETS.

15. The apparatus of claim 13, wherein said actuator means further comprises:
an actuation circuit, operably connected to said transmitter means, for generating said series of digital pulses in response to the closure of an actuation switch.

16. The apparatus of claim 13, wherein said actuator means further comprises:
an actuation circuit, operably connected to said transmitter means, for generating said series of digital pulses in response to the closure of an accelerometer switch.

17. The apparatus of claim 16, wherein said accelerometer switch will close in response to an acceleration that exceeds a threshold, said threshold selectable from the range 2–5 g's.

18. The apparatus of claim 16, wherein said actuation means is mounted in association with an elastic band, said elastic band adapted to be worn on said patient's body.

* * * * *